United States Patent [19]

Hasegawa et al.

[11] Patent Number: 5,041,425

[45] Date of Patent: Aug. 20, 1991

[54] ANTITUMOR AGENT

[75] Inventors: Shin Hasegawa, Pasadena, Calif.; Luke K. T. Lam, North Oaks, Minn.

[73] Assignee: Toyotama Perfumery Co., Ltd., Tokyo, Japan

[21] Appl. No.: 372,432

[22] Filed: Jun. 23, 1989

[30] Foreign Application Priority Data

Sep. 16, 1988 [JP] Japan .................. 63-231668

[51] Int. Cl.$^5$ .............. A61K 31/70; A61K 31/35; A61K 31/34
[52] U.S. Cl. .................. 514/32; 514/453; 514/461
[58] Field of Search ........ 514/32, 450, 453, 461; 536/18.1; 549/275, 268; 424/195.1

[56] References Cited

U.S. PATENT DOCUMENTS 4,479,972  10/1984  Soukup et al. ............. 426/590 X

OTHER PUBLICATIONS

Cancer Research 38, 4486–4495, Dec. 1978, by Benson et al.
Cancer Research 40, 2820–2823, Aug. 1980, by Wattenberg et al.
J. Med. Chem. 30, 1399–1403, 1987, by Lam et al.
Journal National Cancer Institute 68, No. 3, 493–495, Mar. 1982, by Sparnins et al.
Journal National Cancer Institute 60, No. 3, 605–609, Mar. 1978, by Speier et al.
Khodzhimatov, *Chem. Abs.*, 78, 26426d (1973).
He et al., *Chem. Abs.*, 109, 156041u (1988).

*Primary Examiner*—John W. Rollins
*Attorney, Agent, or Firm*—Flynn, Thiel, Bouetll & Tanis

[57] ABSTRACT

A specified citrus limonoid such as limonin and nomilin is isolated from the citrus and is found to be useful to treat a tumor. It is useful as an additive to food.

18 Claims, No Drawings

ANTITUMOR AGENT

The invention relates to an antitumor agent of citrus limonoids.

DESCRIPTION OF THE PRIOR ART

Limonin and nomilin, along with other limonoids, are present in Rutaceous plants which include the common edible fruits; orange, lemon, lime, and grapefruit. The molecular structure of limonoids contains a furan moiety to which a highly oxidized triterpene is attached at the 3 position. Furan-containing natural products such as kahweol and cafestol isolated from green coffee beans have been found to inhibit chemically induced neoplasia. The inhibitory action of these and other classes of anticarcinogens has been attributed, at least in part, to their capacity to induce increased activity of the detoxifying enzyme glutathione S-transferase (GST) see Sparnins, V. L., P. L. Venegus and L. W. Wattenberg. J. Natl. Cancer Inst. 68:483–496 (1982) and A. M Benson, R. P. Batzinger, S. Y. L. Ou, E. Bueding, Y. N. Cha and P. Talalay. Cancer Res. 38:4486–4495 (1978). The furan moiety in kahweol and cafestol has been determined as the functional group that is responsible for the induction of increased GST activity in laboratory animals see L. K. T. Lam. V. L. Sparnins and L. W. Wattenberg. J. Med. Chem. 30:1399–1403 (1987).

SUMMARY OF THE INVENTION

Since limonoids such as limonin and nomilin are furan-containing natural products that are regularly consumed by the general population, we have determined the GST inducing activity of these limonoids and found that the latter compound is a potent enzyme inducer while the former was marginally active. This study correlates the enzyme inducing activity with the inhibition of BP-induced forestomach tumor by limonin and nomilin in ICR/Ha mice.

The invention provides a pharmacological composition which comprises a pharmacologically effective amount of a citrus limonoid and a pharmacologically acceptable carrier. Among the citrus limonoids, limonin and nomilin are especially effective. The composition is useful to treat tumors.

The invention further provides a method for treating a cancer, that is, treating and inhibiting a tumor by administering to a person suffering from the cancer and tumor a pharmacologically effective amount of a citrus limonoid. The citrus limonoids of the invention are useful as anti-tumor agents. The invention relates to the use of the citrus limonoids as an anti-tumor agent and the use of them to manufacture an anti-tumor agent.

In the invention the above specified citrus limonoids, such as limonin and nomilin, are isolated from the citrus and are found to be useful to treat a tumor. They are useful also as an additive to food. They serve as a bitter tasting component.

The invention is in particular useful to treat, inhibit and prevent the gastric tumors.

37 species of the limonoids are available from citrus and are found to have a furan group in their respective structure. Among the limonoids, limonin and nomilin are isolated as the most effective components. Limonin and nomilin are defined by the following formulae (1) and (2), respectively. In the structures, the furan group is attached at its 3-position to a highly oxidized triterpene group at the position of C-17. Also they exist, in citrus, in the form combined with glucose, shown by the formulae (3) and (4), respectively.

(1) limonin

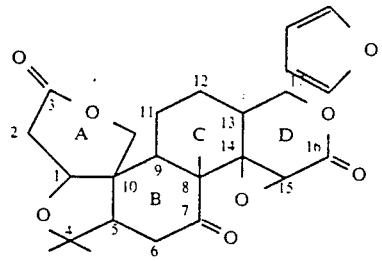

(2) nomilin

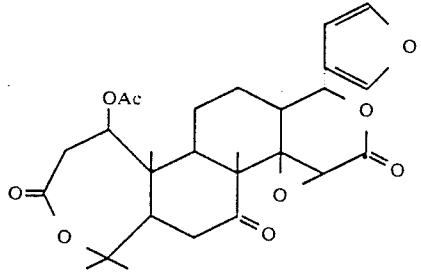

(3) limonin 17-O-β-D-glucopyranoside

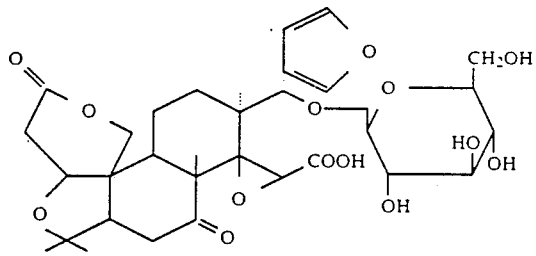

(4) nomilin 17-O-β-D-glucopyranoside

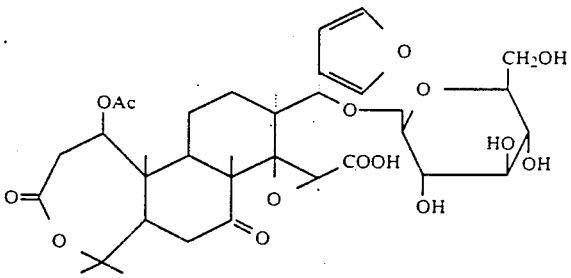

The limonoids such as limonin and nomilin are bitter principles found in common edible citrus fruits. Nomilin when given 3 times at 5 and 10 mg per animal every two days induced increased glutathione S-transferase activity 2.48 and 3.44 times over the control, respectively, in the liver of female ICR/Ha mice. The increase of GST activity in the small intestinal mucosa was 3.00 and 4.17, respectively, over the control. Limonin when given at the same dose levels was not active in the liver. Marginal activity was obtained, however, in the small intestinal mucosa. The more active enzyme inducer, nomilin, was found to inhibit benzo(a)pyrene-induced neoplasia in the forestomach of ICR/Ha mice. The number of mice with tumors was reduced from 100 to 72% and the number of tumors per mouse was significantly decreased as a result of nomilin treatment. Limonin, which is a weak enzyme inducer, was less potent as an inhibitor of benzo(a)pyrene-induced neoplasia. These findings suggest limonoids as a class of regularly consumed natural products may be effective chemopreventive agents.

When the compound of the present invention is used as the anti-tumor agent, it is usually given by the oral administration or parenteral administration (intramuscular or subcutaneous administration). The dose is not particularly limited and it varies depending on the type of the disease, symptoms, age, conditions and body weight of the patient, another treatment conducted simultaneously with this treatment, if any, the frequency of the treatment and the quality of the desired effect. Usually when it is given to adults by oral administration, the dose is about 1 to 100 mg, preferably about 2 to 20 mg and particularly about 8 to 10 mg a day. It is given once or several times a day. When it is given by injection, the dose is about 0.01 to 1 mg/kg, preferably about 0.03 to 0.1 mg/kg.

The agent of the invention is in the form of, for example, powders, fine grains, granules, tablets, capsules, suppositories or injections. In the formulation, an ordinary carrier is used and an ordinary preparation method is employed.

An oral solid preparation is prepared by adding an excipient and, if necessary, a binder, disintegrator, lubricant, colorant, corrigent, etc. to the active ingredient and shaping the mixture into tablets, coated tablets, granules, powder or capsules by an ordinary method.

The excipients include, for example, lactose, corn starch, white sugar, glucose, sorbitol, crystalline cellulose and silicon dioxide. The binders include, for example, polyvinyl alcohol, polyvinyl ether, ethylcellulose, methylcellulose, acacia, tragacanth, gelatin, shellac, hydroxypropylcellulose, hydroxypropylstarch and polyvinylpyrrolidone. The disintegrators include, for example, starch, agar, gelatin powder, crystalline cellulose, calcium carbonate, sodium hydrogencarbonate, calcium citrate, dextrin and pectin. The lubricants include, for example, magnesium stearate, talc, polyethylene glycol, silica and hardened vegetable oils. The colorants include those accepted as colorants for medicines. The corrigents include, for example, cocoa powder, menthol, aromatic powder, peppermint oil, borneol and cinnamon powder. These tablets and granules can be suitably coated with sugar, gelatin, etc.

In the preparation of the injection, additives such as a pH adjusting agent, buffering agent, stabilizer or solubilizer are added, if necessary, to the active ingredient and an intravenous injection is prepared therefrom by an ordinary method.

PHARMACOLOGICAL TEST

Limonin and nomilin were each tested in view of the potent enzyme inducer and inhibition of the gastric tumor induced by benzopyrene.

BP (benzo(a)pyrene) and CDNB (1-chloro-2,4-dinitrobenzene) were purchased from Aldrich Chemical Co. (Milwaukee, WI). 3-BHA (3-tert-butyl-4-hydroxyanisole) was purified by recrystallization from commercial BHA (Sigma Chemical Co., St. Louis, MO). Glutathione was purchased from Sigma Chemical Co. Limonin and nomilin were isolated from grapefruit seeds as follows. Seed meals were washed thoroughly with hexanes and the limonoids were extracted with acetone. Limonin was obtained by fractional crystallization from the mixture in dichloromethane and nomilin was obtained by crystallization from the residue in acetone. Their structures were confirmed by NMR spectral analysis.

CYTOSOL PREPARATION

Female ICR/Ha mice, eight weeks old from Harlan Sprague Dawley Laboratory (Indianapolis, IN), were fed semipurified diet (ICN Nutritional Biochemical, Cleveland, OH) for one week before they were divided into experimental and control groups—three mice per group. The experimental groups were given three doses of the test compounds suspended in cottonseed oil every other day. The control group was given cottonseed oil alone. Twenty-four hours after the last intubation, the mice were killed by cervical dislocation and the liver, lung, forestomach, and the mucosa of the proximal $\frac{1}{3}$ of the small intestine were removed for enzyme preparation. The tissues were homogenized in 1.15% KCl solution by means of a Brinkman homogenizer. The cytosol after $100,000 \times g$ centrifugation for one hour was obtained and frozen at $-80°$ until used. The protein concentration of the samples was determined by the method of Lowry. Each sample represents one tissue from each individual animal.

GST ASSAY

The activity of cytosolic GST was determined according to the method of Habig et al. employing CDNB as the substrate. The rate of reaction was monitored at 340 nm in a Hewlett Packard HP8450A spectrophotometer. Assays were performed at 30° in 0.1M phosphate buffer, pH 6.5, in the presence of 5 mM GSH and 1 nM CDNB. Complete assay mixture without enzyme was used as the control.

TUMOR INHIBITION

Tumor inhibition experiments were carried out according to previously published procedures. One hundred and twenty female ICR/Ha mice (Harlan Sprague Dawley, Indianapolis, IN), eight weeks of age, were divided equally into six groups. The mice were given semipurified diet one week before the start of the experiment and were fed the same diet until three days after the last dose of carcinogen treatment. BP was given by po intubation 2 times a week for 4 weeks at 1 mg (in 0.2 mL corn oil) per dose. The inhibitors were given by po intubation three times a week on days other than the carcinogen treatment. Three additional doses of inhibitors, 2 before the 1st dose and 1 after the last dose of carcinogen were administered. Three days after the last dose of BP, the animals were returned to normal laboratory chow until the termination of the experiment. Eighteen weeks after the first dose of BP the mice were killed and the stomachs were removed and fixed by ig injection of formalin. They were then cut open longitudinally. Tumors of the forestomach were counted under a dissecting microscope with a mm scale. Tumors that were 0.5 mm or larger were recorded and checked histopathologically.

STATISTICAL ANALYSIS

The significance of the number of tumor bearing mice was analyzed by the Chi Square test. The tumor per mouse and enzyme assay statistics were analyzed by Student's t test.

RESULTS

Table 1 shows the inducing effects of limonin and nomilin on the activity of GST in the liver and small intestinal mucosa of ICR/Ha mice. In both tissues the known enzyme inducer and anticarcinogen, BHA, was included as a positive control. Nomilin, at 5 and 10 mg per dose, induced increased GST activity 2.48 and 3.44 times over the control, respectively, in the liver of mice. At the same dose levels limonin was not active. In the small intestinal mucosa, which is a more sensitive tissue in response to inducers, the increased activities of GST by 5 and 10 mg nomilin were 3.00 and 4.17 times, respectively, over the control. In this tissue, limonin showed marginal activity (1.33 and 1.36 times over the control) as an enzyme inducer.

The potency as inhibitors of BP-induced forestomach tumors in ICR/Ha mice was positively correlated with the enzyme inducing activity of these compounds. Table 2 shows the inhibitory effects of limonin and nomilin on BP-induced neoplasia of the forestomach of mice. At 10 mg dose, 72% of the animals had tumors compared with 100% of the animals in the control group. As a positive control the known inhibitor, BHA, was included in this experiment. In this group, 69% of the animals were found to have forestomach tumors. The inhibition by both 10 mg nomilin and 7.5 mg BHA was significantly different from the control. The number of tumors per mouse was also significantly reduced in the 10 mg nomilin group. The 5 mg nomilin group, although showing a slight decrease in the number of animals having tumors, was not statistically different from the control. The same results were obtained with the two dose levels of limonin.

Tables 3 and 4 show how some species of limonoids induce the GST activity on tissues of small intestinal mucosa and liver.

DISCUSSION

A significant number of inhibitors of chemical carcinogenesis have been found to induce increased activity of the detoxifying enzyme GST. The results in this study further confirm the correlation with the naturally occurring limonoids. The enzyme inducing and carcinogenesis inhibiting actions of nomilin were found to be equal in magnitude to those of BHA with the doses employed in this experiment. Since the molecular weight of nomilin is three times higher than BHA the biological activity of the former is estimated to be higher than that of the phenolic antioxidant on a molar basis. Longer dietary administration of these limonoids may produce better inhibitory action against BP-induced neoplasia.

Nomilin, a more effective inhibitor of chemical carcinogenesis than limonin, is present in citrus juices in lower concentration than the latter. The ratio of limonin and nomilin in citrus juices depends on a number of factors which include the variety of the fruit, the season of harvest, the time after the juice is made, and whether the juice has been subjected to heat treatment. In general, the concentration of limonin is 5 to 10 times higher than that of nomilin. The bitterness of limonin can be tasted when its concentration in the juice is greater than 6 ppm. The general consumption of these two limonoids, consequently, is not very high. Preliminary data on other structure-related limonoids, however, indicated similar enzyme inducing activity. It is anticipated that those compounds are also effective chemopreventive agents. Thus the cumulative effect of limonoids and limonoid-like natural products may be substantial.

Limonoid glucoside is hydrolyzed in the intestine through virus to produce corresponding limonoids, which are absorbed into the intestine. The limonoid glucoside in soluble in water and is not so bitter. This is the reason the glucoside is more applicable in the invention.

TABLE

Effects of Limonin, Nomilin and Butylated Hydroxyanisole on the Activity of Glutathione S-transferase in the Tissues of Female ICR/Ha Mice

| Compounds | Dose[b] (mg) | Liver GST Activity[c] ($\mu$mol/min/mg protein) | Ratio (Test/Control) | Small Intestinal Mucosa GST Activity[c] ($\mu$mol/min/mg protein) | Ratio (Test/Control) |
|---|---|---|---|---|---|
| Control | — | 1.15 ± 0.19 | — | 0.33 ± 0.04 | — |
| BHA[a] | 7.5 | 5.24 ± 0.6[d] | 4.55 | 1.08 ± 0.03[d] | 3.25 |
| Limonin | 5 | 1.29 ± 0.35 | 1.12 | 0.45 ± 0.08[f] | 1.33 |
| Limonin | 10 | 1.24 ± 0.23 | 1.08 | 0.45 ± 0.09[f] | 1.36 |
| Nomilin | 5 | 2.86 ± 0.60[e] | 2.48 | 1.00 ± 0.03[d] | 3.00 |
| Nomilin | 10 | 3.96 ± 0.81[e] | 3.44 | 1.39 ± 0.15[d] | 4.17 |

[a]3-tert-Butyl-4-hydroxyanisole (Sigma Chemical Co., Recrystallized from hexanes-acetone).
[b]Limonin and nomilin were given as fine suspension in 0.3 mL cottonseed oil. BHA was readily soluble in cottonseed oil. Control was given cottonseed oil only.
[c]The GST activity was determined according to the method of Habig et al. using CNDB as the substrate Mean ± S.D (n = 3).
[d]$p < 0.001$
[e]$P < 0.005$
[f]$P < 0.05$

TABLE 2

Effects of Limonin and Nomilin on BP-induced Neoplasia of the Forestomach of ICR/Ha Mice[a]

| Compounds | Dose[b] (mg) | No. of mice[c] | No. of mice with tumors[d] | % of mice with tumors | No. of tumors/mouse[e] |
|---|---|---|---|---|---|
| CONTROL | — | 18 | 18 | 100 | 3.6 ± 0.8 (3.6 ± 0.8) |
| BHA | 7.5 | 16 | 11 | 69[f] | 1.7 ± 0.4[g] (2.5 ± 0.4) |
| Limonin | 5 | 16 | 14 | 88 | 3.1 ± 0.8 (3.5 ± 0.8) |

TABLE 2-continued

Effects of Limonin and Nomilin on BP-induced Neoplasia of the
Forestomach of ICR/Ha Mice[a]

| Compounds | Dose[b] (mg) | No. of mice[c] | No. of mice with tumors[d] | % of mice with tumors | No. of tumors/mouse[e] |
|---|---|---|---|---|---|
| Limonin | 10 | 19 | 16 | 84 | 2.5 ± 0.6 (3.0 ± 0.7) |
| Nomilin | 5 | 18 | 15 | 83 | 2.3 ± 0.4 (2.7 ± 0.4) |
| Nomilin | 10 | 19 | 13 | 72[f] | 1.7 ± 0.4[g] (2.3 ± 0.4) |

[a]BP (1 mg/0.2 mL of corn oil) was administered by p.o. intubation twice a week for 4 weeks.
[b]Inhibitors in 0.3 mL corn oil in the form of homogeneous solution (BHA) or fine suspension were administered by p.o. intubation 3 times a week for 4 weeks.
[c]Indicates effective number of mice at the termination of experiment.
[d]All tumors > 0.5 mm were included.
[e]Mean ± S.E.. Numbers in parenthesis indicate number of tumors per tumor-bearing mouse.
[f]$P < 0.025$
[g]$P < 0.05$

TABLE 3

Small Intestinal Mucosa

| Compounds | Dose (mg) | GST Activity (μmol/min/mg protein) | Ratio TEST/CON | P |
|---|---|---|---|---|
| Nomilin | 10 | 2.09 ± 0.32 | 2.77 | <0.005 |
| Deacetylnomilin | 10 | 0.80 ± 0.10 | 1.06 | >0.4 |
| Obacunone | 10 | 1.24 ± 0.05 | 1.65 | <0.001 |
| Issobacunoic acid | 10 | 1.26 ± 0.06 | 1.67 | <0.001 |
| Limonol | 10 | 0.89 ± 0.10 | 1.18 | >0.05 |
| Deoxylimonin | 10 | 0.74 ± 0.03 | 0.98 | >0.50 |
| Ichangin | 10 | 1.10 ± 0.20 | 1.45 | <0.05 |
| CONTROL | — | 0.75 ± 0.02 | — | |

TABLE 4

Liver

| Compounds | Dose (mg) | GST Activity (μmol/min/mg protein) | Ratio TEST/CON | P |
|---|---|---|---|---|
| Nomilin | 10 | 6.05 ± 1.08 | 2.74 | <0.005 |
| Deacetylnomilin | 10 | 3.12 ± 0.62 | 1.41 | >0.05 |
| Obacunone | 10 | 5.55 ± 0.76 | 2.51 | <0.005 |
| Issobacunoic acid | 10 | 7.77 ± 0.39 | 3.52 | <0.001 |
| Limonol | 10 | 2.65 ± 0.45 | 1.20 | >0.20 |
| Deoxylimonin | 10 | 2.31 ± 0.21 | 1.05 | >0.50 |
| Ichangin | 10 | 4.04 ± 0.69 | 1.83 | <0.02 |
| CONTROL | — | 2.21 ± 0.21 | — | |

We claim:

1. A method of treating a patient who has received internally a chemical carcinogen capable of being detoxified by glutathione S-transferase which comprises: administering internally to the patient a pharmacological composition comprising a citrus limonoid in combination with a pharmacologically acceptable carrier, said citrus limonoid being administered in an amount which is effective to increase the chemical carcinogen detoxifying activity of glutathione S-transferase in the patient's body and thereby increase the capacity of the body to inhibit the neoplastic effects of chemical carcinogens.

2. A method as claimed in claim 1 in which said citrus limonoid is limonin or limonin glucoside.

3. A method as claimed in claim 1 in which said citrus limonoid is nomilin or nomilin glucoside.

4. A method as claimed in claim 1 in which said pharmacological composition is administered parenterally.

5. A method as claimed in claim 4 in which said citrus limonoid is administered by injection in an amount of from 0.01 to 1 mg/kg.

6. A method as claimed in claim 4 in which said citrus limonoid is administered by injection in an amount of from 0.03 to 0.1 mg/kg.

7. A method as claimed in claim 1 in which said pharmacological composition is administered orally.

8. A method as claimed in claim 7 in which said citrus limonoid is administered in an amount of from 1 to 100 mg/day.

9. A method as claimed in claim 7 in which said citrus limonoid is administered in an amount of from 2 to 20 mg/day.

10. A method as claimed in claim 7 in which said citrus limonoid is administered in an amount of from 8 to 10 mg/day.

11. A method of increasing the detoxifying activity of glutathione S-transferase in the body of a patient, which comprises administering to the patient an amount of a citrus limonoid effective to increase the detoxifying activity of glutathione S-transferase.

12. A method as claimed in claim 11 wherein said citrus limonoid is selected from the group consisting of limonin and limonin glucoside.

13. A method as claimed in claim 11 wherein said citrus limonoid is selected from the group consisting of nomilin and nomilin glucoside.

14. A method as claimed in claim 11 wherein said citrus limonoid is selected from the group consisting of deacetylnomilin, obacunone, issobacunoic acid, limonol, deoxylimonin and ichangin.

15. A method as claimed in claim 13 in which said agent is administered parenterally or orally in an amount of from 2 to 20 mg/day.

16. A pharmacological tablet or capsule comprising an orally administrable, solid, pharmaceutical carrier and a citrus limonoid selected from the group consisting of nomilin and nomilin glucoside.

17. A pharmacological composition as claimed in claim 16 in the form of a tablet.

18. A pharmacological composition as claimed in claim 16 in the form of a capsule.

* * * * *